United States Patent [19]

Gutierrez

[11] Patent Number: 4,604,245
[45] Date of Patent: Aug. 5, 1986

[54] PERFUME DISPENSING DEVICE

[76] Inventor: D. Arturo M. Gutierrez, Paseo Pinter Rosales, 38, 28008-Madrid, Spain

[21] Appl. No.: 730,323

[22] Filed: May 3, 1985

[30] Foreign Application Priority Data

May 18, 1984 [ES] Spain .................................. 279.366

[51] Int. Cl.⁴ .............................................. B01F 3/04
[52] U.S. Cl. ...................................... 261/26; 261/30; 261/DIG. 65; 422/306; 239/59
[58] Field of Search ................... 261/26, 30, DIG. 65; 422/306; 239/59

[56] References Cited

U.S. PATENT DOCUMENTS

| | | | |
|---|---|---|---|
| 2,737,572 | 3/1956 | Ernst | 422/306 |
| 3,006,042 | 10/1961 | Calandra | 422/306 |
| 4,067,692 | 1/1978 | Farris | 261/DIG. 65 |
| 4,197,271 | 4/1980 | Fenstermaker et al. | 422/306 |
| 4,271,092 | 6/1981 | Sullivan et al. | 422/306 |
| 4,339,079 | 7/1982 | Sato et al. | 422/306 |
| 4,432,938 | 2/1984 | Meetze, Jr. | 422/306 |
| 4,518,404 | 5/1985 | Vaillant et al. | 261/DIG. 65 |

Primary Examiner—Tim Miles
Attorney, Agent, or Firm—Bucknam and Archer

[57] ABSTRACT

A perfume dispenser particularly suitable for cars, is insertable in a housing provided in the front panel or dashboard of a car. It comprises a structure formed by a plate or front panel, with its perimetric border rounded. On the surface of the plate have been cut on one side orifices in which are housed respectively a switch and a pulsator, and on the opposite side, an orifice of greater diameter. From the edge of the orifice an extension forms a cylindrical housing provided with an internal wall; divided into two zones by an intermediate transversal wall provided with a broad central orifice. In the zone of the internal wall in the rear of the transversal wall have been cut two broad rectangular notches in diametrically opposite positions, so that the zone of the internal wall in front of the transversal wall has two broad rectangular notches in diametrically opposite positions. The cylindrical space defined by the transversal wall and the zone in front of the internal wall contains the perfuming product.

8 Claims, 1 Drawing Figure

U.S. Patent  Aug. 5, 1986  4,604,245
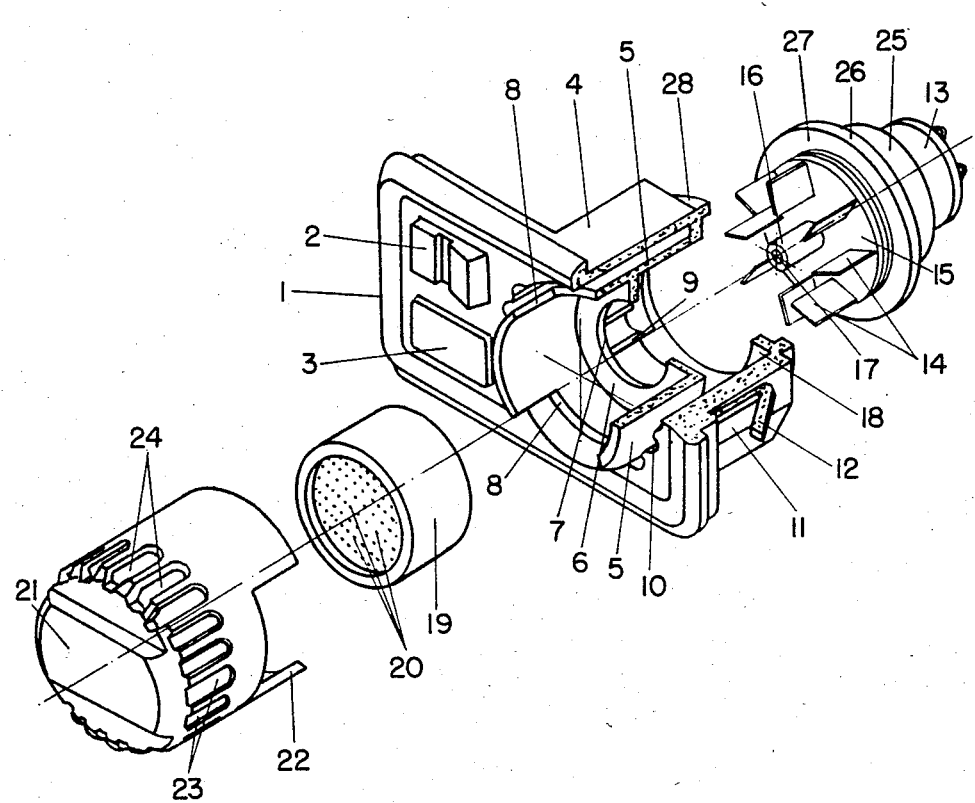

PERFUME DISPENSING DEVICE

BRIEF DESCRIPTION OF THE INVENTION

The present application for Utility Model relates to a panellable perfume dispenser for cars of timed and/or manual operation, which furnishes essential novelty characteristics, as well as notable advantages, over the means heretofore known and used for this same purpose.

The use of perfume-dispensing devices in the car is a fact that is known by everybody, with the object of creating more pleasant ambiental conditions for the driver. This is due to the that that unpleasant odors frequently permeate the interior of the vehicle, which emanate either from the exhaust gases or from the exterior. All this is further aggravated in the case of vehicles used by smokers in which the smell of tobacco lingers inside the car even days after the vehicle has been used, and especially in winter when the outside temperatures compel driving with the car windows closed or almost closed.

These unpleasant odors inside the car make driving or the presence inside the vehicle uncomfortable, so that most drivers frequently resort to the installation inside the car of certain devices which provoke emanations of perfumed products which counteract the presence of unpleasant odors and create a more pleasant ambient.

The devices actually used for the proposed objectives consist generally of recipients which incorporate an aromatic pellet and which gradually provide the desired aromatization to the ambient. This type of devices almost always have the drawback in that these are sited inside the car. Some are actually provided with a magnetic base so as to secure them in place, by attraction, on a metallic part, which does not keep them from coming loose with the continued use of the vehicle, whereas in other cases they are provided with an adhesive which permits securing them in the selected place of the car, but with the drawback that the mark left by the adhesive is always difficult to remove.

There are other types of perfume-dispensing devices for the car which consist of strips impregnated with the odoriferous substance and which dangle, by means of suction pads, principally from the windshield. This has the drawback in that it is uncomfortable to handle, and frequently come loose, and in some cases they can even impair the visibility of the driver.

All the known types of perfume dispensers for the car also have the common drawback in that, independently of their use or positioning in the car, they are in one way or another subjected to air currents which cause premature wear of the aromatizing substance.

The present invention proposes the creation of a device which, correcting the drawbacks of the actually known aromatizing means, permits dispensing in the interior of the vehicle an exact quantity of aromatizing product, according to the desires of the person using it.

Another advantage provided by the perfume dispenser of the present invention consists in the fact that upon attaining the desired ambient, it can be closed or disconnected, thereby prolonging the duration of the aromatizing product.

One other advantage of the perfume dispenser of the present invention consists in that it is of timed actuation, with controllable time periods.

Another additional advantage of the device of the present invention consists in that the same is adaptable to the dashboard of the car, avoiding its detachment and the influence on the same of the air currents.

The device proposed by the present invention relates to a lamellar base or front plate which incorporates, to one of its parts, an electric switch and a pulsator, and on the opposite part a broad orifice. Bordering this orifice is a cylindrical wall projecting backwardly, and in the proximities of the rear border of said wall is a second wall, also cylindrical and in the interior of the first one, projecting forwardly parallel to the previous one, the front edge of which becomes positioned on a plane anterior to that of the front plate itself, with a cylindrical space divided at an intermediate point by a transversal wall, in the interior of which will be housed, on both sides of the aforesaid transversal wall, an electric motor provided with some air impeller blades and the proportioning means of the desired aromatization. Said transversal wall has an orifice in its central zone.

Between the aforesaid second cylindrical wall and the front plate is a peripherical separation space, which permits the coupling of a front closing lid, which has been provided with a plurality of longitudinal openings which, facing broad notches proviced in said cylindrical wall, permit the perfuming product to flow outside.

The unit also includes a timer electronic circuit which commands the electric motor at preset time intervals.

Additional objects and advantages of the invention will become apparent as the following detailed description of the invention is read in conjunction with the accompanying drawing which illustrates a preferred embodiment of the invention.

BRIEF DESCRIPTION OF THE DRAWING

The single drawing shows a perspective view, with partial section of the front plate, a breakdown of the elements comprising the object of the invention.

DETAILED DESCRIPTION OF THE INVENTION

As illustrated in said drawing, the perfume dispenser proposed by the present invention consists of a front lamellar plate 1, in which has been provided, conveniently secured thereto, a switch 2 and a pulsator 3 in parallel positions. On the opposite side of the front plate 1 has been cut a broad orifice from the rear border of which projects, backwardly, a cylindrical wall 4. From the proximities of the rear border of said wall 4 starts a second wall 5, likewise cylindrical, maintaining a certain separation from the wall 4 and extending parallel thereto, the front edge of which passes through the orifice of the lamellar plate 1 up to a plane anterior to that of said plate.

The wall 5 defines a cylindrical space divided by a transversal wall 6 provided with a central orifice 7. On the other hand, on both sides of this transversal wall 6 the aforesaid cylindrical wall 5 shows, in opposite positions, broad rectangular recesses 8 and 9. Lastly, between the cylindrical wall 5 and the front plate 1 is a separation space for housing of the edge of the front closing lid which will be hereinafter described.

From the rear surface of the front plate start securing means of the perfume-dispensing unit to a support, for example, the dashboard of the car, consisting of rear extensions 11, perpendicular to the plane of the front plate, situated on both sides of said front plate, and the final spans of which 12 bend forwardly, at an angle of approximately 135°, thereby forming the attachment means.

In the interior space of the wall 5, situated in the rear of the transversal wall 6, is housed a unit comprised by an electric motor 13, a set of blades 14 actuated by the drive shaft of the aforesaid motor 13, and an intermediate piece 25. The blades 14 are solidly linked to a plate 15 which has in its center a cylindrical elevation 16 provided with a longitudinal orifice 17 by means of which is coupled, preferably by pressure, the drive shaft of said electric motor 13. The intermediate piece 25 is, in general, cylindrical in shape and has a circular rim 26 of greater diameter which gives rise to the seat 27.

In the interior space of the cylindrical wall 5 existing in front of the transversal wall 6 is housed the aromatizing product used with the perfuming device of the invention. In the illustration of the hereinabove described drawing, the aromatizing product is enclosed in the interior of a cylindrical container 19, provided on both bases with a plurality of orifices 20 for the air inflow and outflow.

As experts in the matter will understand, the use of this type of containers must not be absolutely considered as limited in scope, since in the aforesaid housing can be inserted any type of sublimable aromatizing pellet or any other aromatizing means which may be deemed convenient.

Lastly, the perfume dispenser of the invention has been provided with a lid 21 for the front closing of the cylindrical wall defined by the wall 5. This lid 21 is likewise generally cylindrical in shape, its exterior base closed and its lateral wall provided with broad rectangular recesses 22 in frontal positions.

On the lateral wall of the lid 21 have been provided a plurality of parallel longitudinal grooves, evenly distributed around it, which start from the external base and extend up to at least half the height of the lid. A part of these grooves are internally closed (grooves 23 in frontal positions) and the rest are passers (grooves 24 in frontal positions).

The electronic circuit provided for its inclusion with a perfume-dispensing device of the description (not shown herein) is not the object of the invention, and consequently any timer circuit of the known type, which is adequate for the proposed objectives, may be used. The preferred position for this circuit will be by the rear part of the front plate 1, facing the position occupied by the switch 2 and the pulsator 3.

For the formation of the perfume-dispensing device of the invention, the unit formed by the electric motor 13, the intermediate piece 25 and the set of blades 14, is inserted in the interior space of the wall 5, in the rear of the transversal wall 6, with this unit secured in its positioning, by pressure, by means of the internal edge 18 of said cylindrical wall 5 and also through the pressure exerted by the interior wall of the end area 28 on the peripherical surface of the circular rim 26 provided in the intermediate piece 25. The seat 27 of this intermediate piece 25 acts as arrester in the insertion movement of the aforesaid unit, upon reaching the rear wall of the rim 18. In this manner, the edges of the blades 14 that are more distant from the base 15 are thereby positioned in the proximities of the rear surface of the transversal wall 6. Upon inserting the aromatizing product, packed according to 19 or in any other form, in the cylindrical housing in front of the transversal wall, the lid 21 can then be placed therein, enclosing in its interior the cylindrical wall 5 and housing its edges in the space 10 existing between said cylindrical wall 5 and the front plate 1. Upon making the corresponding connections between the timer circuit (not shown herein) and the terminals of the electric motor 13, the device of the invention is ready for use.

The perfume dispenser as hereinbefore described will be placed in a convenient part of the car, preferably on the dashboard, so that access to the same will be easy and comfortable for the driver. The anchoring thereof is carried out by means of hooking paws comprised by the extensions 11, the final spans 12 of which give way elastically in the insertion movement in the support, subsequently recuperating so as to attach the unit in its position once it has been completely inserted in its housing, all this facilitated by light attenuations of the material provided in the bending zones.

Feeding will be effected from any point at which the battery voltage is present. Upon making the pertinent connections, actuating the switch up to its on position, the device will operate automatically, every time that a time period controlled by the electronic timer elapses.

The pulsator 3 is used as a test pulsator, in such a manner that upon connecting the unit by means of the switch 2, if the aforesaid pulsator 3 is activated, it will provoke the immediate start-up of the motor.

If it is desired to provide the interior of the vehicle with a certain initial aromatization, the pulsator 3 will be actuated several times, thereby provoking the start-up of the motor as often as said pulsator is actuated.

The blades 14 are driven by the electric motor 13. Thus, every time that the motor starts functioning, the set of blades 14 impels air through the central orifice of the transversal wall 6, with this impelled air passing through the aromatizing means 19 and dragging therewith the emanation provided by the latter. The air with the aromatizing emanations reaches the exterior through the recesses 8 of the cylindrical wall 5 and the passer grooves 24 of the lid fronting said recesses 8.

The control of the quantity of air flowing outside the perfume-dispensing device is possible as a function of the number of passer grooves 24 facing the recesses 8. With the simple turn of the lid 21, it is possible to modify the number of grooves 24 by which air is supplied with the perfuming product, and therefore greater or lesser air outflow, to the point of being able to shut off passge of this air completely if the closed grooves 23 are only the ones facing the opposite recesses 8.

The air drawn in by the set of blades 14 penetrates the recesses 9 of the cylindrical wall 5, facing the recesses 22 of the lid 21. In the locking position of the lid, the recesses 9 and 22 will not be facing each other, thus making impossible the suction of air on the part of the aforesaid set of blades.

The timer device has been hereinbefore described simply as a means to start the electric motor 13 at preset time intervals. However, these time intervals between two successive actuations can be controlled at different durations, for the purpose of adapting the demands of each particular case. Likewise, the electronic circuit will be provided with means that will permit controlling the duration of each actuation, so as to permit a more or less rapid ambientation.

Another characteristic of the invention consists in that the timer circuit is prepared to keep the electric motor 13 operating during a time in proportion to the number of time that the pulsator 3 is actuated and/or in proportion to the times that the aforesaid pulsator 3 is kept activated. This characteristic is particularly useful at the initial utilization time of the vehicle, so as to obtain a fast ambientation of the interior thereof.

Although certain preferred embodiments of the invention have been herein described in order to illustrate the principles of the invention, it will be understood that certain modifications in structure can be effected, likewise protected, which may affect the shape, size or fabrication materials of the unit or of its parts, or any others which do not alter the embodiment of the invention.

I claim:

1. Panellable perfume dispenser for cars of timed and/or manual operation, insertable in a housing provided for such purpose in the front panel or dashboard of a car, characterized because it comprises a structure formed by a plate or front panel, with its perimetric border rounded and increased frontally in weight, on the surface of which have been cut, on one part, sundry orifices in which are housed respectively a switch and a pulsator, and on the opposite part, an orifice of greater diameter from the edge of which starts towards the interior an extension which forms a cylindrical housing provided with an internal wall, parallel to that of the cylindrical extension and separated therefrom, divided into two zones by an intermediate transversal wall provided with a broad central orifice, so that in the zone of the internal wall in the rear of the aforesaid transversal wall have been cut two broad rectangular notches in diametrically opposite positions, whereas the zone of the internal wall in front of said transversal wall likewise has two broad rectangular notches in diametrically opposite positions.

2. Panellable perfume dispenser as defined in claim 1 and further characterized because the cylindrical space defined by the aforesaid transversal wall and the zone in front of said internal wall is capable of containing in its interior the perfuming product, with this space closing frontally by means of a likewise cylindrical lid, adaptable to the zone in front of the internal wall simply by pressure, said lid provided with a plurality of longitudinal grooves distributed evenly throughout its periphery, from which start passer grooves which occupy diametrically opposite positions, whereas internally it has been provided with two notches facing each other and positionable at will coinciding with the notches of the zone in front of the internal wall.

3. Panellable perfume dispenser as defined in claim 1 and further characterized because in the zone in the rear of of the internal wall is housed, by pressure, a tiny electric motor drive shaft of which actuates a set of air induction blades towards the interior of the unit, and the terminals of which are joined, preferably by welding, to a printer circuit plate on which has been mounted a timer circuit for the actuation of said electric motor.

4. Panellable perfume dispenser as defined in claim 3 and further characterized because the aforesaid timer circuit is adjustable at will both in the period of time elapsing between two successive actuations and in the duration of said actuations.

5. Panellable perfume dispenser as defined in claim 1 and further characterized because the actuation of the pulsator immediately starts the aforesaid motor.

6. Panellable perfume dispenser as defined in claim 3 and further characterized because said timer causes the continued actuation of the motor as often as the number of times that the pulsator has been actuated.

7. Panellable perfume dispenser as defined in claim 3 and further characterized because the duration of the actuation of the motor is in proportion to the time that the aforesaid pulsator is kept activated.

8. Panellable perfume dispenser as defined in claim 1 and further characterized because the unit is attached to the dashboard of the car by means of two diametrically opposite paws parallel to the aforesaid interior extension, formed by means of sundry projections from the same plate or front panel which interbend, attenuated in the bending zones in order to give them greater elasticity in the insertion and removal operations of the unit.

* * * * *